United States Patent [19]
Roof

[11] 3,935,097
[45] Jan. 27, 1976

[54] ACID AND ALCOHOL CARRIER FOR HF-H₂O CHROMATOGRAPHIC SEPARATION USING ANION EXCHANGE RESIN

[75] Inventor: Lewis B. Roof, Bartlesville, Okla.
[73] Assignee: Phillips Petroleum Company, Bartlesville, Okla.
[22] Filed: Aug. 7, 1974
[21] Appl. No.: 495,509

[52] U.S. Cl. ............................................. 210/31 C
[51] Int. Cl.² ......................................... B01D 15/08
[58] Field of Search .......... 210/31 C, 25; 55/67, 71

[56] References Cited
OTHER PUBLICATIONS
Introduction to Modern Liquid Chromatography by Snyder and Kirkland, John Wiley and Sons, New York, N. Y., pp. 287–307 and 318–325.

*Primary Examiner*—John Adee

[57] ABSTRACT

HF and water are separated in a high pressure liquid chromatographic column using a mixture of a saturated aliphatic carboxylic acid such as formic acid and a saturated aliphatic alcohol such as methanol as the carrier. This is of particular utility in continuous control of an HF alkylation unit.

10 Claims, 2 Drawing Figures

ACID AND ALCOHOL CARRIER FOR HF-H₂O CHROMATOGRAPHIC SEPARATION USING ANION EXCHANGE RESIN

BACKGROUND OF THE INVENTION

This invention relates to a high pressure liquid chromatography.

High pressure liquid chromatography and its forerunner, paper chromatography, have been known for many years. These techniques along with gas chromatography make possible a myriad of separations which would otherwise be difficult or impossible. One separation of potential commercial importance which has been difficult to carry out in the past is the separation of HF and water in the system acid of an HF alkylation unit.

SUMMARY OF THE INVENTION

It is an object of this invention to separate HF and water; it is a further object of this invention to monitor the HF and water in the system acid of an HF alkylation unit; it is yet a further object of this invention to provide an improved HF alkylation control system; it is still yet a further object of this invention to separate HF, water, and acid soluble oil (partially fluorinated heavy hydrocarbons); and it is still yet a further object of this invention to provide an improved high pressure liquid chromatographic separation.

In accordance with this invention HF and water are separated in a high pressure liquid chromatographic column using a mixture of a saturated aliphatic carboxylic acid and a saturated aliphatic alcohol as the carrier in a column having a weakly basic anion exchange resin as the packing.

BRIEF DESCRIPTION OF THE DRAWING

In the drawings, forming a part thereof.

DESCRIPTION OF THE PREFERRED EMBODIMENTS

Figure 1:
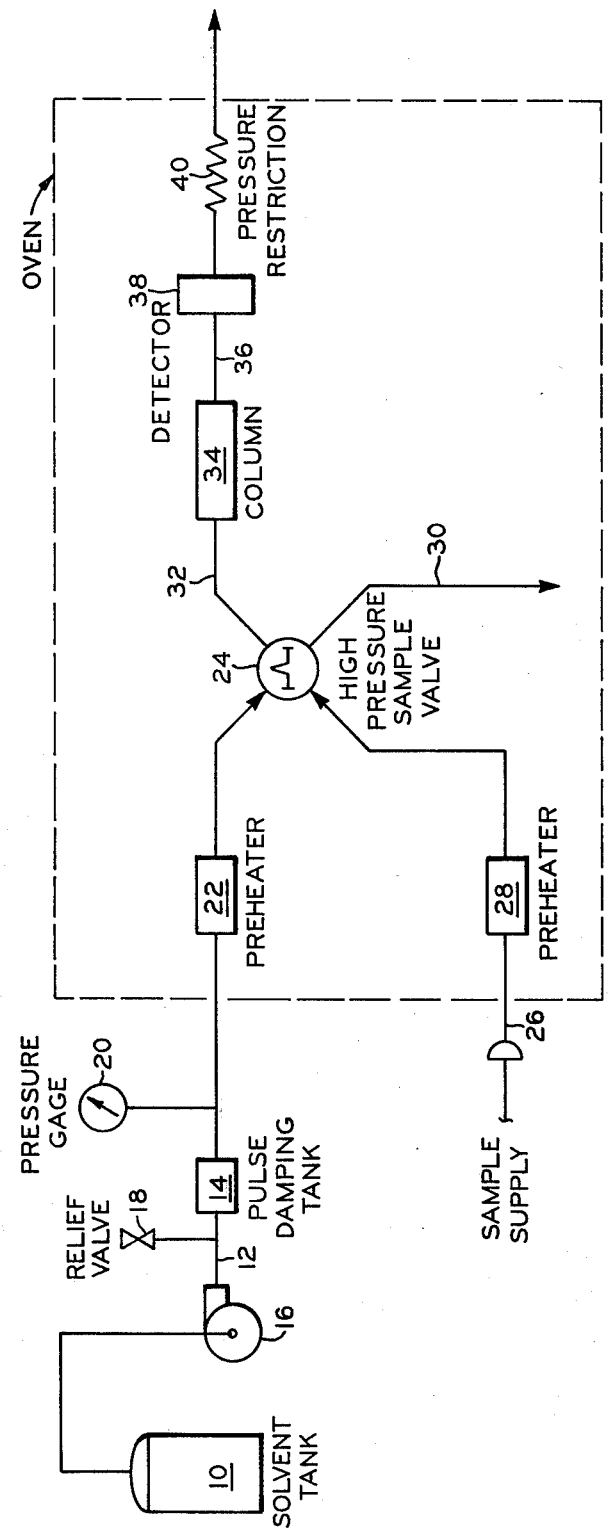
FIG. 1 is a schematic representation of a monitoring system of this invention.

The invention is of particular applicability in the control of an HF alkylation operation such as that shown in Chapman, U.S. Pat. No. 3,478,125 issued Nov. 11, 1969, the disclosure of which is hereby incorporated by reference. The system acid is that coming out of the bottom of the settler and being returned to the reaction zone. The sample is withdrawn at a point prior to combining this stream with a stream of fresh makeup HF. Analysis of this stream can be utilized to determine how well the re-run unit or acid purification unit is cleaning up the acid. The output signal may control such parameters as flow rate, temperature, or pressure of the re-run unit.

Generally the system acid will contain about 90 to 94 weight per cent HF, 1 to 3 weight per cent water, and 1 to 3 weight per cent heavy partially fluorinated hydrocarbons (acid soluble oils) and 2 to 6 weight per cent light hydrocarbons.

The high pressure liquid chromatographic column can be a column such as the Optichrom LC high pressure liquid chromatography system sold by Applied Automation, Inc., Pawhuska Road, Bartlesville, Oklahoma. The sample and solvent are passed through a sampling valve which allows sample to be continually passed through the valve except when it is switched to allow a small portion of sample which is trapped to be introduced into the carrier stream and thus into the column under high pressure. This type of high pressure sample valve for chromatography is known in the art and is described in U.S. Pat. No. 3,387,496 issued June 11, 1968, to A. B. Broerman, the disclosure of which is hereby incorporated by reference.

The pressure in the column will generally vary from 200 to 1800 psi with the flow rate being ¼ to 5 cc/min., and the operating temperature within the range of 40°F to 400°F. The flow is usually at a fixed rate to assure a uniform sample, about 0.5 to 4, preferably about 1 to 2 cc/minute being satisfactory.

The solid packing is a weakly basic anion exchange resin such as AG3-X4A produced by Bio-Rad Laboratories, Richmond, California. This resin comprises a styrene-divinylbenzene polymer to which polyalkylamine groups are attached.

The packing is preferably prepared by first flowing water and sodium hydroxide through the resin to remove chlorine ions. Next the alkanecarboxylic acid and water is flowed through to remove sodium hydroxide. Finally, the saturated aliphatic alcohol is flowed through the material prior to its use. Preferably the resin is soaked in the carrier prior to adding it into the column so as to avoid expansion of the column.

The carrier liquid must be a mixture of a saturated aliphatic carboxylic acid and a saturated aliphatic alcohol, preferably a mixture containing 0.2 to 2 moles of acid per liter of alcohol.

The saturated aliphatic carboxylic acid can be any normally liquid saturated aliphatic carboxylic acid but is preferably formic, acetic or propionic acid because of their lower viscosity. Thus the exchange resin, if not already in that form is converted to the formate, acetate, or propionate form in the preferred embodiments. Similarly the aliphatic alcohol can be any normally liquid saturated aliphatic alcohol but is preferably methanol, ethanol, or n-butanol, most preferably methanol because of the lower viscosity. Mixtures of either the acids or the alcohols or both can also be used.

The detector can be either a refractive index type, an ultraviolet absorber or a density type. Preferably a density type which does not require the use of glass which is etched by the HF is utilized.

Such a detector can be constructed as follows. An oval tube is disposed with the long direction thereof in a vertical plane, said tube having a conduit communicating therewith at a top portion of the oval extending downwardly to a differential pressure cell and a similar conduit at a bottom portion of the oval extending upwardly to said differential pressure cell, with means to introduce effluent from a chromatographic column to a central portion of a flat side portion of the oval and means to remove material from a corresponding central portion of the conduit forming the other flat side of the oval. The apparatus is liquid full to begin with and as effluent from the chromatographic column flows into the first port, it is split in substantially equal volumes upwardly and downwardly through the conduit forming the first flat side of the oval. Any change in composition of the column effluent, such as occurs when a constituent of the sample appears from the effluent, results in a change in the differential pressure measured by the differential pressure cell. It has been found that adequate sensitivity for such analyses can be obtained when the total vertical height of the conduits connecting the upper and lower portions of the oval with the differential pressure cell is as small as four inches wherein the conduits are of a diameter as small as 18 mils. However, greater sensitivity can be obtained by increasing the vertical lengths of the conduits to provide a differential measuring system of greater heights. The differential pressure cell measures the pressure differential which exists between the upper region of the oval and the lower region of the oval. This differential pressure cell can advantageously be a variable reluctance transducer having a center diaphragm which separates the conduits connecting with the upper and lower portions of the oval. The displacement of the diaphragm in either direction changes the relative electrical properties of coils on the two sides of the diaphragm. These coils are connected to a measuring circuit such as that available from Validyne Engineering Corporation, 18819 Napa Street, North Ridge, California 91324. Such an apparatus is capable of measuring pressure differentials as small as 0.05 psi, for example. Alternatively a reference fluid and a carrier fluid containing the effluent from a chromatographic column can be passed on opposite sides of a differential pressure measuring means so as to measure pressure differential exerted by predetermined heights of the reference fluid and sample-containing fluid in conduits in communication with opposite sides of the pressure measuring means. For instance the reference fluid can be passed upwardly past one side of the pressure measuring means and thence to a vertically disposed conduit projecting upwardly while the carrier fluid containing the sample is passed through a similar conduit on the other side of the pressure measuring means, the two conduits being joined at the upper end thereof and the resulting mixed fluids passed to vent.

The resolution of water in HF can be controlled by varying the amount of acid in the alcohol solvent. Too small an amount of acid makes the separation time too long. Too much, while giving a short time for the analysis will not make an adequate separation between the peaks. The optimum can easily be determined experimentally for any given installation.

It is to be noted that by using a nonaqueous base solvent, the water can be measured. Also since the HF is eluted last, better measurement of the minor water peak is allowed.

Referring now to the drawings, particularly FIG. 1, there is shown a solvent supply tank 10 for storing the formic acid/methanol solvent. Solvent is passed via line 12 through pulse damping tank 14 by means of pump 16. Relief valve 18 is set at about 1800 psi to relieve the pressure if it exceeds the capacity of the column. For convenience pressure gauge 20 allows a visual check of the pressure. The solvent then goes to solvent preheater 22 and thence through high pressure sample valve 24. Sample supply from the settling column of an HF alkylation unit is introduced via line 26 through sample preheater 28 to high pressure sample valve 24. Both preheaters 22 and 28 are contained in the heated oven. This supply of sample can be taken off continuously and vented to the atmosphere via line 30 except when it is desired to analyze a sample. At this point, sample valve 24 is switched so as to trap a small portion of the sample flowing therethrough and introduce same into line 32 along with the carrier solvent. The sample is then carried by means of the solvent liquid via line 32 to column 34. Column 34 is packed with an ion exchange resin which has been treated with sodium hydroxide to remove chlorine ions and thereafter with formic acid. Coming out of column 34 is line 36 which carries the eluted portions of the sample to detector 38 which in this case is a differential density detector. Capillary back pressure rate restrictor 40 helps to maintain pressure within the detector.

The sample valve is returned to its original position whereby the sample flows through the same and to vent via line 30 as soon as the trapped sample therein has been carried into the column. The carrier solvent drives the sample through the column.

The preheaters, sample valve, column, and detector are preferably located within an oven so as to minimize variations due to temperature changes.

Many conventional parts such as temperature controllers, frame elements, valves, and the like have been omitted for the sake of simplicity but their inclusion is understood by those skilled in the art and is within the scope of the invention.

EXAMPLE

Figure 2:
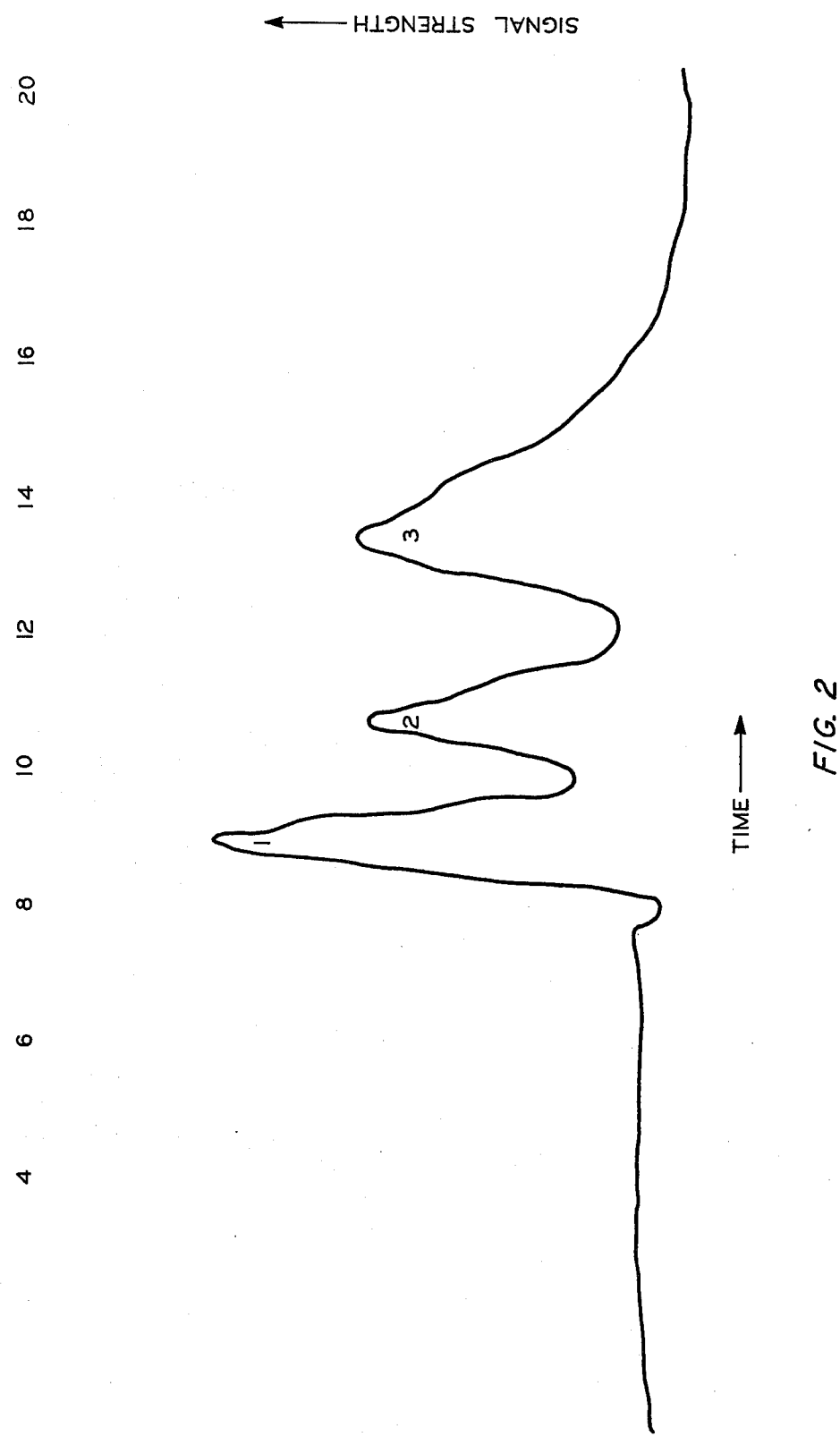
FIG. 2 is a curve showing a typical separation utilizing the invention.

System acid from the settling column of an HF alkylation unit similar to that shown in said patent, U.S. Pat. No. 3,478,125 was passed to a preheater and thence through a high pressure sampling valve such as is shown in FIG. 1. A solvent liquid comprising one liter of methanol with 1.5 molar formic acid was used as a carrier liquid. This liquid was passed through a preheater and thence to said high pressure sample valve. The column was 6 foot long, ¼ inch outside diameter Monel tubing packed with weakly basic anionic exchange resin in the formate form produced by treating Bio-Rad resin No. AG3-X4A, which is a weakly basic anion exchange resin comprising polyalkylamine functional groups attached to a styrene-divinylbenzene polymer lattice, with sodium hydroxide and thereafter with formic acid in water and thereafter with methanol. The flow rate of solvent through the column was two cc per minute. The column temperature was 50°C. The system acid contained about 92 weight per cent HF, 2 weight per cent water, 2 weight per cent acid soluble oils (mostly partially fluorinated heavy hydrocarbons) and 4 weight per cent light hydrocarbons. A sample of the system acid was trapped in the high pressure sample valve and passed into the carrier liquid. Downstream of the column was a differential density type detector. The first material to come through the column was the combined light hydrocarbons and acid soluble oils labeled peak 1 in FIG. 2. Thereafter, the water came through and finally the HF which was labeled peak 3.

Control

A similar separation was attempted utilizing a strong base anion resin borate form. No separation of water from HF occurred.

While this invention has been described in detail for the purpose of illustration, it is not to be construed as limited thereby but is intended to cover all changes and modifications within the spirit and scope thereof.

What is claimed is:

1. A process for separating HF, water, and acid soluble oil comprising passing a sample containing said HF, water and acid soluble oil through a high pressure liquid chromatographic column packed with a weakly basic anion exchange resin in a carboxylate form utilizing as a carrier a liquid mixture of a normally liquid saturated aliphatic carboxylic acid in a normally liquid saturated aliphatic alcohol.

2. A method according to claim 1 wherein said acid is formic acid and said alcohol is methanol.

3. A method according to claim 2 wherein said formic acid is present in an amount within the range of 0.2 to 2 moles per liter of said methanol.

4. A method according to claim 2 wherein said anion exchange resin is prepared by first treating said weakly basic anion exchange resin with sodium hydroxide, thereafter flowing said formic acid and water therethrough and finally flowing said methanol therethrough.

5. A method according to claim 4 wherein said sample is system acid from an HF alkylation unit.

6. A method according to claim 5 wherein said acid soluble oil is made up of heavy partially fluorinated hydrocarbons and where some light hydrocarbons are present which remain with said acid soluble oil.

7. A method according to claim 6 wherein said system acid comprises 90 to 94 weight per cent HF, 1 to 3 weight per cent water, 1 to 3 weight per cent heavy partially fluorinated hydrocarbons, and 2 to 6 weight per cent light hydrocarbons.

8. A method according to claim 7 wherein said column is operated at a temperature of 40°F to 400°F and a pressure of 200 to 1800 psi.

9. A method according to claim 8 wherein the materials eluted from the column are analyzed by means of a differential density detector.

10. A method according to claim 9 wherein an HF re-run column of said HF alkylation unit is controlled in response to the amount of HF, water and acid soluble oil detected.

* * * * *